United States Patent
Bjornson et al.

(10) Patent No.: US 6,900,889 B2
(45) Date of Patent: May 31, 2005

(54) SUBMERSIBLE LIGHT-DIRECTING MEMBER FOR MATERIAL EXCITATION IN MICROFLUIDIC DEVICES

(75) Inventors: Torleif O. Bjornson, Gilroy, CA (US); Kevin Maher, Woodside, CA (US); Michael Robert Gluszcak, San Jose, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 20 days.

(21) Appl. No.: 10/739,720

(22) Filed: Dec. 18, 2003

(65) Prior Publication Data

US 2004/0165186 A1 Aug. 26, 2004

Related U.S. Application Data

(63) Continuation of application No. PCT/US02/19494, filed on Jun. 19, 2002.
(60) Provisional application No. 60/305,122, filed on Jul. 12, 2001.

(51) Int. Cl.[7] ............................................. G01N 21/05
(52) U.S. Cl. .................... 356/246; 356/436; 356/318; 356/417
(58) Field of Search ........................ 356/344, 317–318, 356/417, 436, 440, 246

(56) References Cited

U.S. PATENT DOCUMENTS

| | | | | |
|---|---|---|---|---|
| 5,039,492 A | * | 8/1991 | Saaski et al. | 422/82.09 |
| 5,530,553 A | * | 6/1996 | Hsia et al. | 356/436 |
| 5,599,503 A | * | 2/1997 | Manz et al. | 422/82.05 |
| 5,995,209 A | * | 11/1999 | Ohman et al. | 356/72 |
| 6,399,952 B1 | * | 6/2002 | Maher et al. | 250/458.1 |
| 6,558,945 B1 | * | 5/2003 | Kao | 435/287.2 |

FOREIGN PATENT DOCUMENTS

WO    WO 01/20309 A1    3/2001

* cited by examiner

Primary Examiner—Richard A. Rosenberger
(74) Attorney, Agent, or Firm—Stephen C. Macevicz; David Albagli

(57) ABSTRACT

A system for material excitation in microfluidic devices is described. Aspects of the invention resemble a submerged periscope when in use. They allow for light to be redirected along a more advantageous trajectory as does the maritime device. A prism with a reflecting surface may be used to direct a laser beam along one or more microfluidic trenches or channels. Alternatively, a reflecting surface may be provided in connection with a simple support. Directing a beam along multiple paths is preferably accomplished by scanning a single laser across or around the reflecting surface provided. Provision may be made for at least a portion of the submersible used to function as an electrode to assist in electrokinetically driving fluids and/or ions within the microfluidic device.

48 Claims, 12 Drawing Sheets

SUBMERSIBLE LIGHT-DIRECTING MEMBER FOR MATERIAL EXCITATION IN MICROFLUIDIC DEVICES

CROSS-REFERENCE TO RELATED APPLICATIONS AND PATENTS

This application is a continuation of and claims priority to International application PCT/US02/19494 filed Jun. 19, 2002, which claims priority to U.S. provisional application Ser. No. 60/305,122, filed Jul. 12, 2001, which applications are each incorporated herein by reference in its entirety.

TECHNICAL FIELD

This relates to systems for detection of material in microfluidic devices. Aspects of the invention provide for direct application of light to excite material within a device to enable fluorescent detection without producing background fluorescence in a chip resulting in signal loss or interference.

BACKGROUND

In performing any one of several useful types of analyses, microfluidic devices may be employed. Whether applied for the purpose of DNA separation or drug screening, the ability to achieve movement of sample, reagents and buffer within a network of fine trenches or channels can result is great time savings over conventional techniques. Most all common laboratory procedures such as mixing, incubation, metering, dilution, purification, capture, concentration, injection, separation, and detection may be performed on a single microfluidic "chip." What is more, the chip format allows for parallel tasking and concomitant gains in productivity.

Data from experiments run on microfluidic devices is commonly extracted utilizing optical detection techniques. Laser-induced fluorescence (LIF) techniques are particularly advantageous. LIF techniques employ laser light to excite material for detection by an optical unit such as a photomultiplier tube (PMT) device or charge-coupled device (CCD) camera. One or more PMT devices or CCD cameras may be used or any combination thereof.

Most often, LIF detection utilizes a laser beam directed normal to the plane of the microfabricated device, exciting molecules at or adjacent to a detection zone. Another detection scheme employs light reflecting structures integrated within a chip to direct a beam across a detection zone. Such an approach may further utilize a second reflector to allow light detection normal to the plane of the microfluidic device.

Irrespective of what advantages such systems provide, they suffer from serious drawbacks. Background illumination or scattering of light introduced at detection windows and less-than-perfect reflecting surfaces often adversely affect sample detection capabilities. Furthermore, for some configurations, the layout will require passing the laser light through the material forming the body or a cover of the microfluidic device. Some configurations impose difficult demands on chip flatness or dimensional tolerances. This may introduce background fluorescence (i.e., autofluorescence) that also decreases detection signal accuracy. More particularly, autofluorescence is the fluorescence generated by the microfluidic device material (e.g., the channel-wall material) upon illumination with the excitation beam. Again, autofluorescence is problematic because it decreases detection sensitivity.

Some have sought to address these problems through material choice to reduce background fluorescence and by use of high-quality optical surfaces to avoid light scattering within chips. Issues associated with cost and reproducibility are presented in either case. The present invention offers an elegant alternative in dealing with either fluorescence or optical challenges.

Further advantages and utility of the present invention may also be apparent to those with skill in the art upon further consideration of the various features of the present invention.

SUMMARY OF THE INVENTION

The present invention includes light-directing hardware, microfluidic devices adapted for use with the same, and combinations thereof. In one variation of the present invention, a light-directing member includes a reflecting surface is sized in coordination with a microfluidic chip so that the end of the light-detecting member may reside within a sample waste well with its reflecting surface set to send light through various channels in the microfluidic device. The location of the reflecting surface (whether provided in connection with a prism or simply with a supporting member) in relation to a chip may be varied. For instance, the light directing member can be provided at any location within the chip where light introduction is desired. The location may be in fluid communication with channels in the chip such that the light directing member can be submersed within liquid media contained therein. In order to set the reflecting surface(s) properly with respect to channels in a device, location features may be variously provided.

Further variation in connection with the optical system described herein includes provision to scan light across a reflecting surface to illuminate multiple channels.

In one variation, the system includes a light directing member, a light source, and one or more movable reflectors positioned in the optical path of the light. By adjusting the angle of the reflector(s), the excitation beam may be selectively sent to a channel or a target region of a channel. The excitation beam is desirably sent through the vertical center of the channel in order to reduce interference arising from light reflecting of the channel walls. The reflector may be held by a rotational actuator such as a galvanometer.

Additionally, the light-detecting member itself or a conductive member or coating associated therewith may be provided to serve as an electrode for I 0 electrokinetically driving material within a microfluidic device.

Additionally, the light may be directed at the microfluidic device from above or below the microfluidic device to strike the reflecting surface of the light directing member. The light may be directed, for instance, through the cover film or through an opening in the body of the microfluidic device. The light may be directed towards the microfluidic device at a 90 degree angle relative to the plane of the microfluidic device.

In another variation, a system includes a microfluidic device having at least one first channel and a reservoir (e.g., a sample waste well) in fluid communication with the first channel; a first light-directing member having a distal end positioned in the reservoir of the device; and a light source. Light from the light source is directed off a reflecting surface of the light directing member to illuminate sample material in a detection zone along the first channel of the microfluidic device. The microfluidic device may further include a sample-flow channel (e.g., a separation channel) fluidly joined to the first channel at the detection zone of the channel. The sample-flow channel is joined at an angle such that light propagating through the detection zone does not enter the sample-flow channel. In one variation, the sample-flow channel is joined to the first channel at an angle ranging from 30 to 60 degrees.

It is to be understood that the present invention includes the devices as well as the methodology disclosed. Furthermore, it is contemplated that any of the features of the systems disclosed, alone or variously combined, comprise aspects of the present invention.

BRIEF DESCRIPTION OF THE DRAWINGS

Each of the following figures diagrammatically illustrates aspects of the present invention. The illustrations provide examples of the invention described herein. Like elements in the various figures often are represented by identical numbering. For the sake of clarity, some such numbering may be omitted.

DETAILED DESCRIPTION

Figure 1:
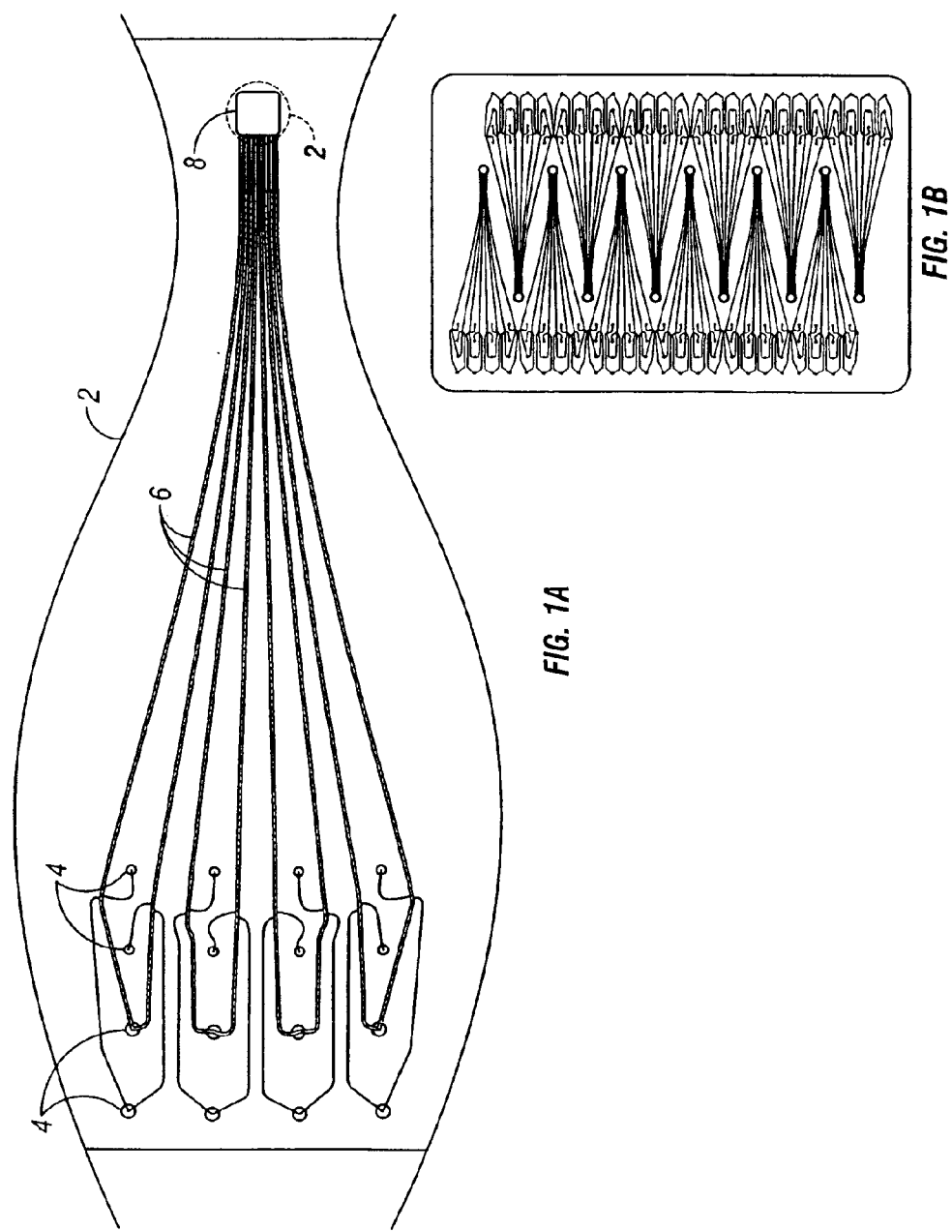
FIG. 1A is a top view of features of a microfluidic device.
FIG. 1B is a top view of a microfluidic device showing a number of functional units.

In connection with the figures, the following text provides examples or variations of the invention. Turning to FIG. 1A, a portion of a chip (2) is shown. It includes a plurality of ingress reservoirs (4) in communication with a plurality of channels (6) which exit into a common waste well (8). Samples reagents added to selected ingress reservoirs are electrokinetically manipulated to carry out various processes as noted above.

Figure 2:
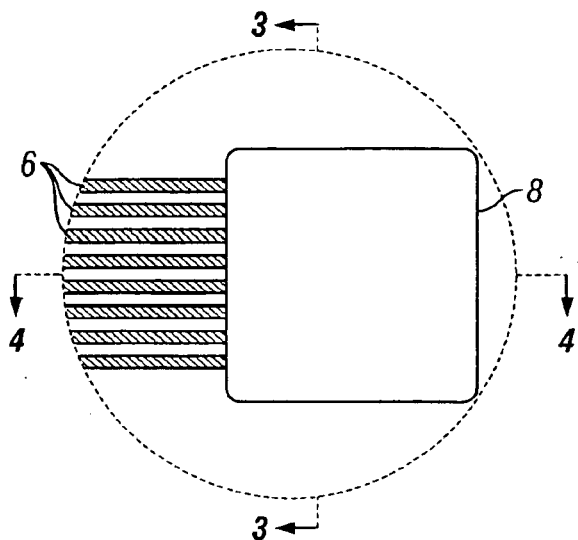
FIG. 2 is a detail of the sample waste well of the device shown in FIG. 1A.
Figure 3:
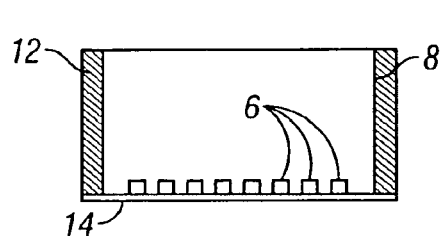
FIG. 3 is a cross-sectional view of the well as shown in FIG. 2 taken along line A—A.
Figure 4:
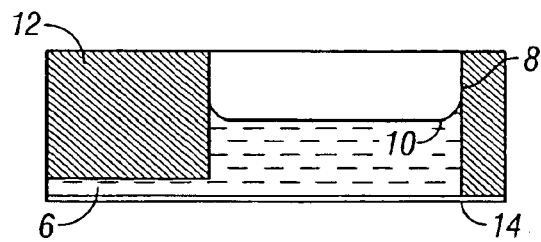
FIG. 4 is a cross-sectional view of the well as shown in FIG. 2 taken along line B—B.

FIG. 2 shows a detail of the chip in the area of the waste well. Multiple channels (6) empty into well (8). FIG. 3 shows the channels end-on as they enter the well. FIG. 4 shows a channel and the well in cross section, with the well partially filled with liquid to form a meniscus (10).

FIGS. 3 and 4 both illustrate a preferred manner of producing chip (2). A chip body (12) defines a portion of each of the aforementioned features, with a base backing or covering (14) affixed thereto that completes the channels and reservoirs/wells.

The microfabricated structure or functional unit shown in FIG. 1A includes eight separation channels (6). Each separation channel is fluidly coupled to three ingress reservoirs (4). This arrangement permits running up to eight separate procedures in parallel in connection with a single waste well (8). Of course, the number of channels in communication with a given waste well (8) may be greater or smaller. For example, only one channel may be so-connected. Alternately, upwards of 20 to 100 channels may empty into a single waste well.

Further, it is contemplated that a number of such functional units as shown in FIG. 1A may be provided on a single chip. The functional units may be positioned on a chip such that adjacent functional units point in opposite directions as shown in FIG. 1B. This configuration is space efficient. The functional units, however, may be otherwise positioned on a chip. For example, the functional units may be positioned such that each functional unit points in the same direction. See, e.g., FIG. 13.

A chip preferably has a thickness (T), width (W), and length (L) of 0.005 to 0.5 inches, 0.5 to 2.5 inches and 1 to 10 inches, respectively. Additionally, certain films may be used as chips and be as thin as 0.005 inches.

Each reservoir (4) is preferably sized to receive sufficient material to run a desired test or experiment and accept an electrode for running the procedure electrokinetically (i.e., employing either or both electrophoretic and electroosmotic phenomena). Suitable materials for the electrodes include platinum or other conducting materials, particularly those resistant to corrosion. The electrodes may be connected to a programmable voltage controller for applying desired voltage differentials across the channels. The electrodes are positioned in the reservoirs such that electrical contact is made with a sample or medium therein suitable for carrying out electrokinetic processes. Exemplary media includes but is not limited to fluids (e.g., buffered solutions, samples, etc.) and gels such as polyacrylamide gel and agarose.

Still, it is noted that aspects of the present invention need not be employed exclusively in connection with an electrokinetic chip. As will be apparent to one with skill in the art, features as described herein may be used in connection with a microfluidic device that is at least partially pressure driven or otherwise motivated.

Regardless, a complete chip is preferably configured to include 96 or 384 wells to correspond in number to such standard microliter plates as available through Van Waters and Rogers and other plate microliter plate manufacturers, conforming to what is known as the SBS standard. Conventional dispenser/pipetter means such as available from Beckman Coulter, Packard Instruments, Zymark, and other dispenser/pipetter manufacturers, are often used with such plates. An advantageous manner in which to configure a chip with the channel layout observed in connection with FIG. 1A is by arranging such functional units in a head-to-toe or complimentary fashion.

Typically, channels (6) will have a rectangular, trapezoidal or "D"-shaped cross-section. However, other cross sectional geometry may be employed. Usually, the channels preferably have a substantially constant or uniform cross-section. Preferably, channels (6) have a height and a width between about 0.1 μm and about 100 μm. It is also preferred that channels have a surface finish that does not result in irregular flow effects.

Chips according to the present invention may be fabricated in any number of manners. Most preferably, a chip body (12) is formed in plastic off of a micromachined/etched positive. Suitable plastics include acrylics, polycarbonates, polyolefins, polystyrenes and other polymers suitable for microfluidic or electrokinetic applications. Backing (14) is preferably made of a nonconducting film attached at the back of the body. One suitable material for backing (14) is a polymethylmethacrylate (PMMA) film. The backing is preferably attached to body by chemical, thermal or mechanical bonding. Ultrasonic welding (an example of the mechanical welding) may also be employed to fuse various parts together. Of course, as is known in the art, the body of microfluidic devices may be produced directly by etching the intended structures in a substrate. In such instances, a cover including wells or reservoirs openings is preferably placed over channels or trenches in the substrate to complete the device. Alternatively, the channel features can be formed in the cover (or film) by e.g., embossing. The film thereafter being attached to a substrate which may feature wells. Further details as to chip construction may be appreciated to those skilled in the art.

As is known in the art, voltages may be used to drive the chip. For example, U.S. Pat. No. 6,010,607 to Ramsey describes information on the manner in which voltages may be applied in order to run chip (2). Other techniques as presently known and used in the art can, of course, also be used in driving chip (2).

Figure 5:
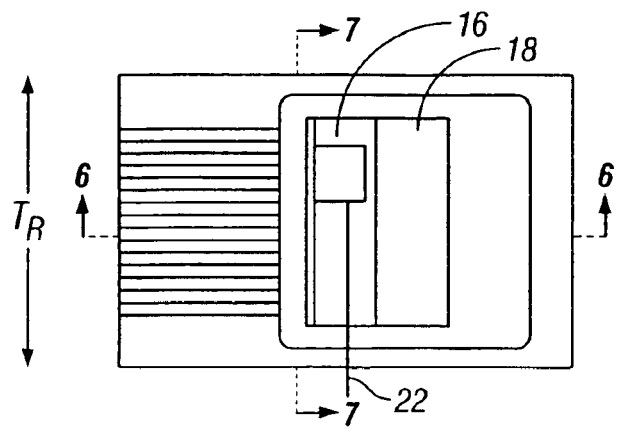
FIG. 5 shows the features in FIG. 2 together with light-directing hardware according to the present invention.
Figure 6:
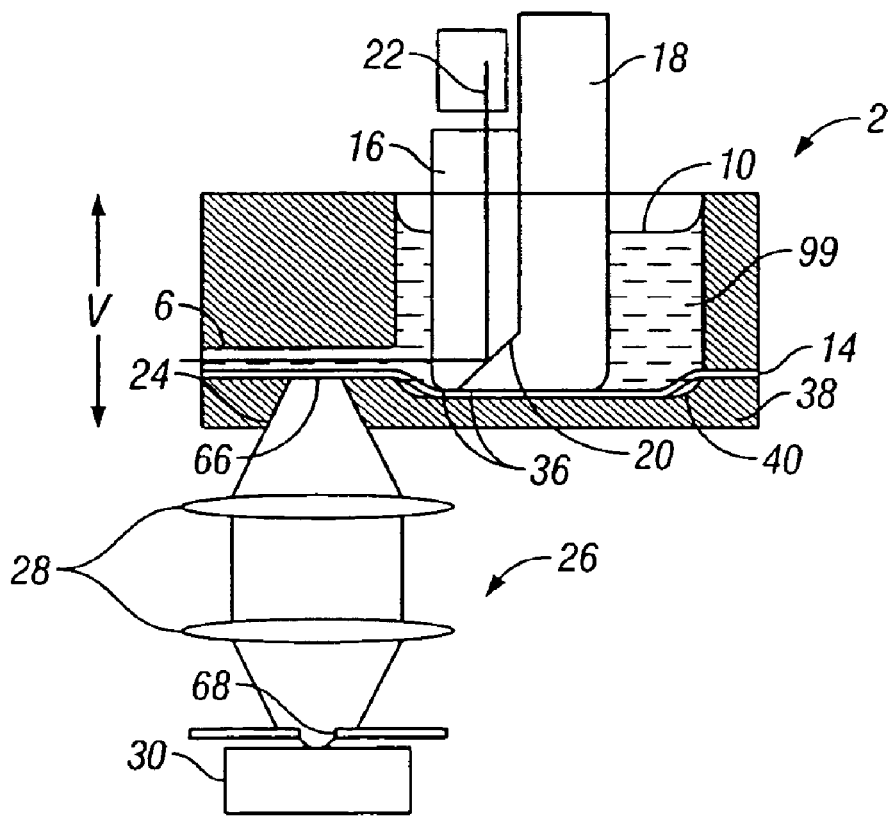
FIG. 6 is a cross-sectional view of FIG. 5 taken along line C—C.
Figure 7:
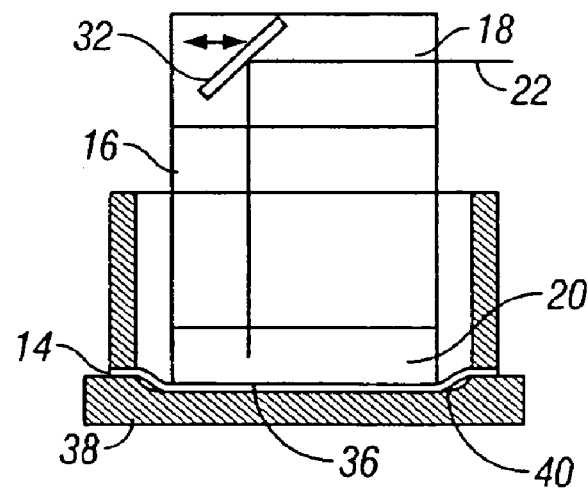
FIG. 7 is a cross-sectional view of FIG. 5 taken along line D—D.

Turning now to FIGS. 5–7, features of the present invention are shown in connection with a portion of a chip as described so far. FIG. 5 is a top view of aspects of the present invention showing the features in FIG. 2 together with light directing members. FIGS. 6 and 7 show side and end views taken along lines C—C and D—D, in FIG. 5. In each, optional prism (16) is backed by an optional support member (18). A reflecting surface (20) is provided. As shown in FIG. 6, these components may be submersed in media (99). Media (99) is contained in the chip as described above.

Reflecting surface (20), may be provided in connecting with prism (16) or support member (18). It may be provided in connection with prism (16) by way of a reflective coating deposited on the angled surface of the prism. The coating chosen should be selected so as to reflect a beam of sufficient intensity to carry out the detection methodology described below. Accordingly, it may be preferred to use aluminum or silver coatings over gold since they absorb a lower percentage of the wavelengths of light produced by such lasers as typically used in detection schemes. However, for other reasons discussed below, it may be more important to utilize a less corrosive material such as gold or platinum for reflecting surface (20). In any event, the material coating may be applied by electroplating, sputter coating or otherwise as would be known to one with skill in the art.

A reflective coating may be applied to the outside of prism (16) or on support (18). If both a support and a prism is to be used, a transparent seal (such as provided by epoxy) may be preferred between the parts if the reflective surface is to be provided on support (18). Passing light through a prism offers an advantage in that it avoids passing light through media contained in a well or reservoir. Accordingly, loss of beam light intensity and fluorescence interaction with this material is avoided. Moreover, passing light though meniscus (10) will not occur, thereby avoiding any lens-type effect this has on beam (22) increasing the difficulty in which is may be directed down the length of fine channels. Indeed, it is for reason of beam divergence that a laser is the most preferred source of light for the invention. The coherent beam offered by such a device allows for greater light intensity as a point of interest for a given distance the light most travels. An alternative method for delivering light to a desired location involves inserting a fiber optic within the well or channel in an orientation to achieve the desired illumination or excitation.

Regardless of whether a prism is used or not, if the reflective surface is to be provided in connection with support (18), it is possible no coating may be required. Instead a polished surface may suffice, so long as absorption effects of the base metal of support (18) is acceptably low.

When a prism is provided, instead of using a coating on the prism for reflective surface (20), it may be provided by selecting parameters sufficient to result in total internal refraction within prism (16) to redirect a beam of light (22) instead. This phenomena is described by the equation:

$$\sin \theta_c = n_2/n_1 \text{(for } n_1 > n_2\text{)}$$

where $\theta_c$ is the minimum angle at which total internal reflection occurs and $n_1$ and $n_2$ are the refractive indices of the material in which total internal reflection is desired and that of the material external to the material within which total internal reflection is desired. Since $n_2$ will approximate the value of water (n=1.33) for most solutions used in well (8), certain design considerations must be taken into account. To utilize a reflection surface angled at 45° relative to the initial beam trajectory, a prism material having a refractive index >1.88 must be used. Accordingly, for such a setup, any one of a number of rare-earth doped glasses may be used. Where a lower refractive index material is desired, such as quartz (n=1.47) or crown glass (n=1.52), the geometry of the prism may be modified, together with mounting structure associated with the light source to accommodate a higher incidence angle. However, a 45° angle of incidence is preferred in each variation of the invention since it turns a beam by 90°, allowing associated hardware to be setup at orthogonal angles.

However provided, in the variation of the invention in FIGS. 5–7, reflecting surface (20) is oriented to reflect a beam (22) along a channel (6) as shown in FIG. 6. In so doing, sample material within channel (6) at and above a detection window (24) is illuminated. This in turn causes tagged, labeled or marked material to fluoresce producing light that may be picked up by a detection system (26). To increase signal and enhance illumination, the sample detection channel may also incorporate certain surface coatings or claddings, or be composed of specific materials such that the channel walls will serve as a waveguide reflecting beam (22) inward. Various detection systems may be employed. For example, a system utilizing one or more lenses and a PMT device or a CCD camera (30) may be employed.

A suitable light collection setup is shown in FIG. 6. In this case, light is collected through lenses (28) from the bottom of the card or chip. The light is imaged through a slit (68) and collected by, for example, a PMT. The slit provides a spatial mask thereby setting the size of a detection region (66). The amount of fluorescent light that is collected from the bottom of the card may thus be controlled by the presence and size of the slit (68). In this manner, an optimum amount of fluorescent light may be collected. Alternatively, sets of pinholes and other variations can be utilized for the mask configurations disclosed herein.

It is also contemplated that slit (68) may be positioned on top of or on the bottom of backing (14). The slit may be, for example, a layer inside the chip or a layer formed on an outside surface. The slit may also be in the form of a coating deposited on the cover film or backing (14).

While the present invention may be utilized to direct a beam up a single channel or trench, it is preferred that provision be made to allow detection in multiple channels running more-or-less simultaneously. This may be accomplished using multiple beams, each aligned to reflect into a given channel. More preferably, it is accomplished by scanning a single beam into a number of channels (or simply directing it across a number of channels). In the latter embodiment, a single beam may be provided normal or transversely to a region of parallel channels or channel streams similar to the configurations disclosed in U.S. Pat. Nos. 5,833,826 and 5,741,412, and WO 01/20309. In the former embodiment, several ways of beam scanning are contemplated, the first of which is most clearly shown in connection with FIG. 7. Here, a mirror (32) to be attached to structure under control enabling it to traverse the face of reflecting surface (20) as indicated is provided. Of course, it is contemplated that mirror (32) and its source may be oriented otherwise. An example of a linear control mechanism for moving the mirror is a voice-coil actuator. Also, other types of actuators and devices may be used to move the mirror relative to the reflecting surface (20) as is known to those of ordinary skill in the art. Feedback control systems may also be incorporated into the system to optimize the position of the mirror (32) relative to the reflecting surface (20).

Figure 8:
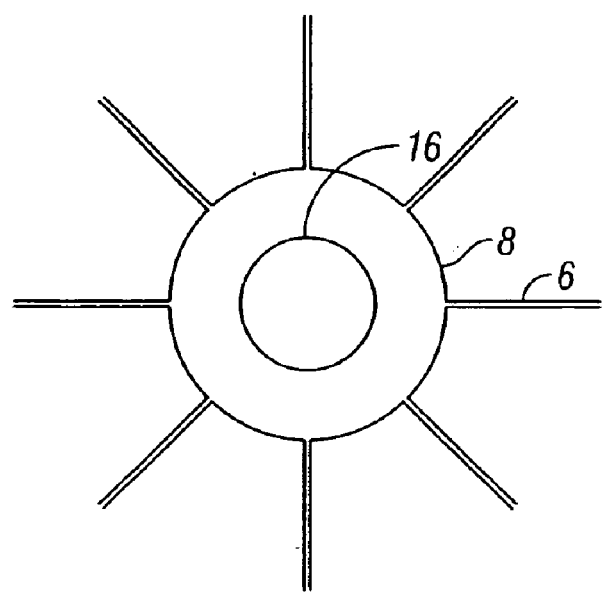
FIG. 8 shows an alternate configuration for a portion of a microfluidic device useable in the present invention.
Figure 9A:
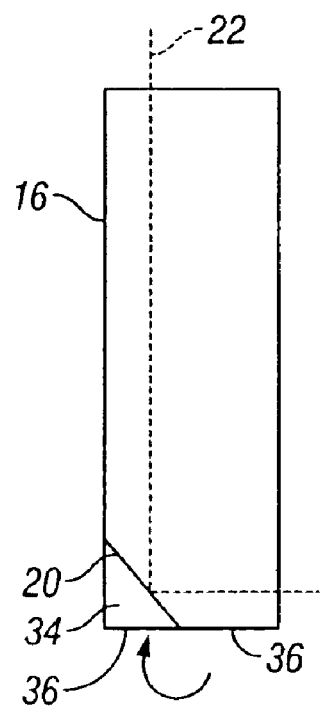
FIGS. 9A and 9B show prism configurations complimentary to the device shown in FIG. 8.
Figure 9B:
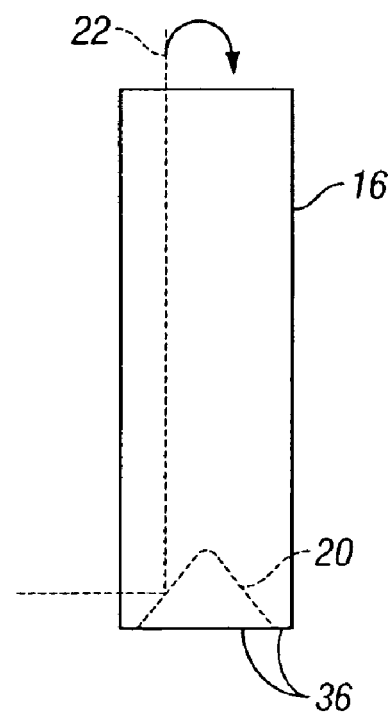

FIGS. 8, 9A and 9B illustrate other manners in which to scan a beam into multiple channels. FIG. 8 shows a channel configuration with a prism (16) located at the center of a waste well (8). In FIG. 8, channels (6) empty into waste well (8) so each has an axis through a center point shared by prism (16). A circular waste well for such a configuration is preferred, but not required. FIGS. 9A and 9B show alternate side views of the prism in FIG. 8.

The prism configuration in FIG. 9A includes a planar reflecting surface (20). The backside (34) of the reflecting surface may be filled in as shown. Alternately, it may be left open. It is advantageously filled in by material such as epoxy to protect any coating on reflecting surface from corrosive interaction with material in well 8. Also, it provides for a cylindrical body. This may be useful since prism (16) in FIG. 9A is preferably placed in well (8) and rotated in order to direct beam (22) into each channel (6) to enable detection when multiple channels are used in parallel. Rotating a cylindrical body rather than one missing a section of material produces less disruption of material within well (8).

The reflecting surface associated with prism in FIG. 9B is configured differently although backspace (34) may, likewise, be filled in with material. This will similarly insulate reflecting surface (20). However, to effect scanning a beam into multiple channels with the inventive variation in FIG. 9B, the beam is rotated instead of the prism. It may be preferred that the conical reflecting surface (20) be faceted in order to avoid divergence of beam (22).

For the variation in FIG. 9B, filling backspace (34) may provide another advantage. Namely, it provides a flat surface at the base of prism (16) useful for positioning reflecting surface (20) with respect to the channels. In order to properly locate reflecting surface to direct a beam up a channel, prism placement can be critical.

Additionally, the reflecting surface (20) and beam (22) may be held fixed relative to one another and the channels may be rotated such that each channel (6) may be aligned with the beam. This may be performed by fixing the prism (16) and the beam (22) and rotating, for example, the microfluidic chip. Rotation of the above mentioned components may be performed in a number of manners including, for example, using a galvanometer-type actuator.

FIGS. 6 and 7 show a manner of accurately and precisely placing reflecting surface (20) to direct a beam as desired. This approach may also be used with the prisms shown in FIG. 9B. Referring to FIGS. 6–7, a base (36) of a prism, support structure or both abuts a portion of chip (2) maintained as a stable location feature. As shown, backing (14) is maintained in a set location by a platen or fixture (38). Backing or cover (14) is shown bowed or flexed into recesses (40) in platen (38). An advantage of such an approach is that the reflected beam may be directed down the channel (6) within the channel walls. Further, by controlling the point that the beam strikes the reflecting surface (20), the reflected beam may be vertically (V) and transversely (Tr) centered in channel (6) minimizing signal interference arising from light striking the walls of the channel. Another advantage of such an approach is the ability to lower the position of reflecting surface (20) with respect to chip (2) so as to be able to bounce a beam off an area inboard of the leading edge of reflecting surface. Further, it allows passing beam deep within the interior of a prism, if used. It also eliminates the requirement to accurately control card thickness.

For chips where the channels are not at the bottom of structure, but rather formed at an intermediate height within a body, a recessed location-function approach may not be most preferred, or even feasible. Instead, it may be desired to simply locate base (36) against the base of a substantially non-deformable portion of the chip. On the other hand, it may be desirable to locate reflecting surface (20) relative to channels in a chip by way of features other than a base (36). For instance, in connection with the prism arrangement shown in FIG. 9A, base (36) is held so it does not contact chip (2). Instead it rotates above backing (14). Accordingly, stop features incorporated in a holding and actuating mechanism can set the height of reflecting surface (20) relative to the chip. Such an approach may also be used in conjunction with prisms or support members that do not move once placed in relation to a chip. Yet another approach is to locate a reflecting surface by reference to any repeatable feature that may be provided in a chip (2) or chip platten (38).

Especially in connection with the variations of the invention shown in FIGS. 5–8, 9A and 9B, an electrode feature may be included with whatever body is submerged in well (8). This may be accomplished by utilizing a conductive material for optional support member (18). Stainless steel, or titanium alloy may be desired for corrosion resistance. Alternately, a coating of gold or platinum may be applied to support (18) so it will resist corrosion. Indeed, a suitably electrically conductive coating may itself function as an electrode even if the underlying material of support (18) is not conductive. Similarly, a conductive coating may be applied to prism (16) so at least a portion of the exterior of this member serves as an electrode. Instead, a simple wire or rod electrode may be affixed to whatever structure prism (16) and/or support member (18) is attached to serve as an electrode for driving chip (2).

Hydrophilic coatings may be applied to prism 16 and/or support member 18. Hydrophilic coatings may be helpful in avoiding bubbles.

With any of the systems described herein, it is noted that mounting and actuating structure for the prism or a supporting member for reflecting surface may be provided to advance the reflecting surface into a recess within a chip. Alternately, a chip may be moved in order to submerge a reflecting surface that is mounted in a stationary fashion. Provision of such constructional detail in the form of collateral structure and control for that structure is within the ability of those within the level of ordinary skill in the art.

Figure 10:
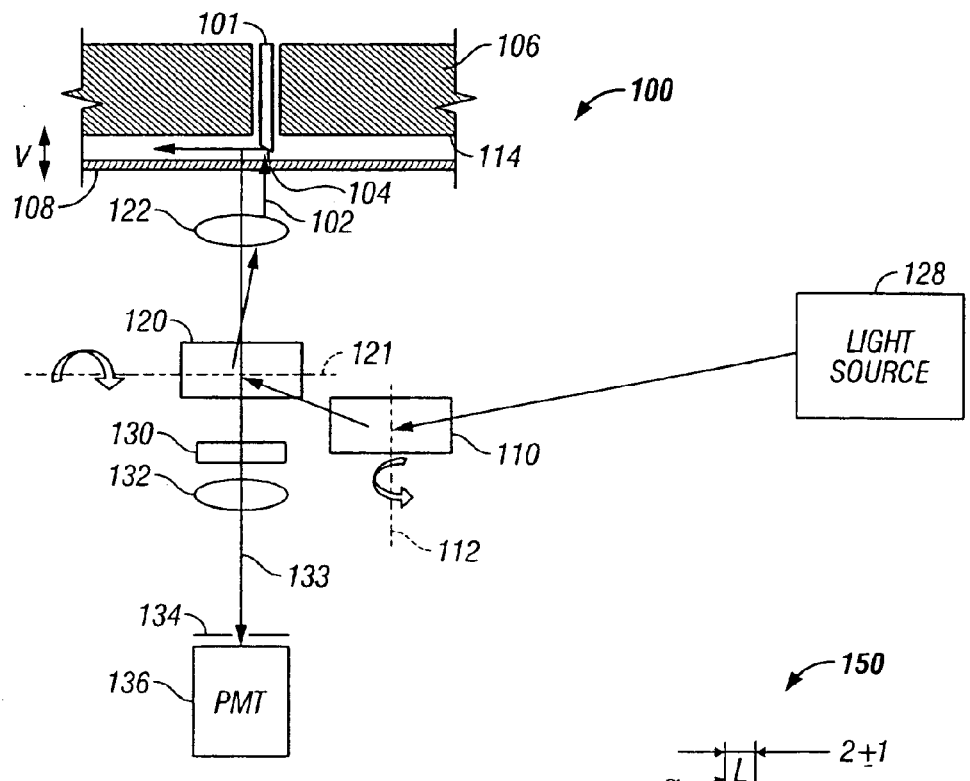
FIG. 10 shows a system including optical hardware and a light directing member according to one variation of the present invention.

FIG. 10 shows another system (100) for illuminating and detecting sample in a channel of a microfluidic device. The system (100) shown in FIG. 10 includes a submersible probe or light directing member (101). The light directing member (101) serves to aim light through the channel (114). Unlike the system shown in FIGS. 5–7, however, the excitation beam (102) of the system shown in FIG. 10 is directed at the reflecting surface (104) from below the microfluidic chip (106). The excitation beam (102) is directed through the backing or cover film (108) before striking the reflecting surface (104).

The optical hardware shown in FIG. 10 includes various components such as a light source (128), a rotatable first mirror (110), a rotatable second mirror (120), and a lens (122). Light from the light source (128) follows an optical path which is adjusted by the above mentioned components to control the point or location that the excitation beam (102) strikes the reflected surface (104), the position of the excitation beam within the channel (114) may be adjusted and axially centered. Vertically (V) centering the excitation beam within the channel (114) reduces interference with the channel walls.

The optical path of the light may be controlled and adjusted by changing the angle of the first mirror (110) and the second mirror (120). The first mirror (110) is rotatable about a first axis (112) which is perpendicular to channel (114). The first mirror directs light from the light source (128) towards the rotatable second mirror (120). The second mirror directs light towards an objective lens (122) which launches the light towards the reflective surface (104). The reflective surface (104) makes an angle with the channel (114) which may range from 10 to 80, more desirably about 45 degrees. The angle should be selected such that the beam can reflect off the reflective surface (104) down channel (114). In this manner, beam (102) illuminates or excites materials in channel (114). Preferably, the reflected light is directed along the channel's central axis or midway between opposing walls defining the channel.

As stated above, the system (100) is adapted to adjust and control the position of the light beam through the channel (114). In particular, vertical (V) control of the light beam in channel (114) is provided by adjusting the angle of the first mirror (110). When the first mirror is rotated about the first axis, the beam follows the above described optical path and strikes the reflecting surface at a point corresponding to the angle of the first mirror. Accordingly, the light reflected into and through the channel (114) may be vertically adjusted by changing the angle of the first mirror about the first axis.

Various apparatuses may be used to move or rotate the mirrors. An example of a rotational actuator to rotate the first mirror is a galvanometer. To reiterate, it is desirable to direct the reflected beam through the vertical center of the channel or midway between the cover film and the channel walls to reduce background and interference. Providing a black card or body also serves to reduce background noise and crosstalk.

The excitation beam may also be adjusted in the transverse direction. As shown in FIG. 10, the second mirror (120) is rotatable about a second axis (121). The second axis (121) is parallel to channel (114) and thus when the second mirror is rotated the excitation beam (102) is directed towards a different target region of the microfluidic device. The transverse adjustment or resolution may be as small 1–10 microns or less. Also, in the case where several parallel channels fluidly connect with one waste well, the second mirror may be rotated to adjust (or step) the beam greater distances up to, for example, ±3.5 mm or more.

In another variation, a lens having a larger field of view such as a telecentric lens may be used in combination with the above described mirrors. Consequently, the light beam may be stepped across greater distances on the chip. For example, light from such a lens may be directed at second light directing members disposed in second waste wells of a second functional unit on the microfluidic device.

Various apparatuses may be used to move or rotate the second mirror. The second mirror may be held by a rotational actuator such as, for example, a galvanometer. However, other mechanisms may be utilized to rotate or otherwise move the mirrors in accordance with the present invention as is known to those of ordinary skill in the art.

The light beam diameter and the lens may also be selected to provide a beam waist that does not contact the card body or cover film, thus reducing background fluorescence. For example, the lens may be a 10× objective microscope lens. The lens may have, for example, a numerical aperture of at least 0.45. An example of a beam waist may be 20 microns. However, the beam may be otherwise designed and still be in accordance with the present invention. Again, it is desirable that the beam not contact the walls of the card or the cover film.

The system shown in FIG. 10 also includes light collecting hardware. The collecting or detecting hardware includes a filter (130), a second lens (132), a slit (134) and a PMT (136). The first lens (122) collects light emitted from a fluorescing sample in the detecting zone or segment of the channel. The emitted light is directed to and through second mirror (120). The second mirror in this construct may be a diachronic mirror such that the light may pass through the second mirror (120). The filter (130) excludes certain wavelength ranges which are not of interest. Finally, a photomultiplier tube (136) is shown receiving the collected light beam (133). The photomultiplier tube (136) may provide a signal corresponding to the concentration of analyte, for example.

Figure 11A:
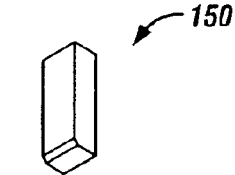
FIGS. 11A–11D show various views of a light-directing member in accordance with the present invention.
Figure 11B:
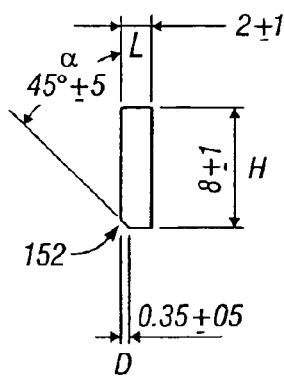
Figure 11C:
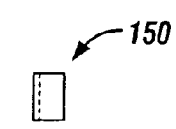
Figure 11D:
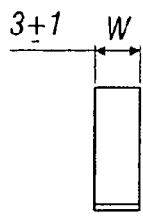

FIGS. 11A to 11D show details of a reflective probe (150) which may be inserted into a waste well or other well to reflect the excitation beam in accordance with the present invention. FIG. 11A shows a perspective view of the reflective probe (150). The probe may be made, for example, from chromium carbide with a diamond machined 45 degree mirror reflecting surface (152). This construction may also provide, if desired, an electrical conductor to electrokinetically drive fluids from one location to another within the channel network.

Additionally, the reflecting surface may have other angles so long as the excitiation beam is reflected into the detection zone properly. Preferably, the beam does not interact or hit the walls of the channel prior to illuminating the material to be excited. Also, cross talk between channels is undesirable as each of these phenomena decreases sensitivity of the detection system.

The construction of the chip itself can also reduce cross talk and increase sensitivity. For example, a chip may be made from black or opaque material which exhibits little background fluorescence. Such a configuration is relatively easy to manufacture. The chip may be molded, for example, using a black material or resin. Also, the cover film enclosing the channels desirably has a low fluorescence.

Referring to FIGS. 11A–11D, the reflective probe (150) may have a generally elongated shape with a reflective surface (152) adjacent the distal end. The height (H) of the probe may range from 5 to 20 mm and perhaps, 5 to 10 mm. A desirable height may be 8±1 mm. The width (W) and length (L) may also vary. The dimension (D) for the reflective surface may range from 100 to 300 um, and perhaps from 0.1 to 1 mm. In the probe shown in FIG. 11B, however, the dimension D is about 0.35±0.05 mm. However, these dimensions may vary and the dimensions of the probe may be selected such that the probe fits within a well of a microfluidic chip.

Figure 12B:
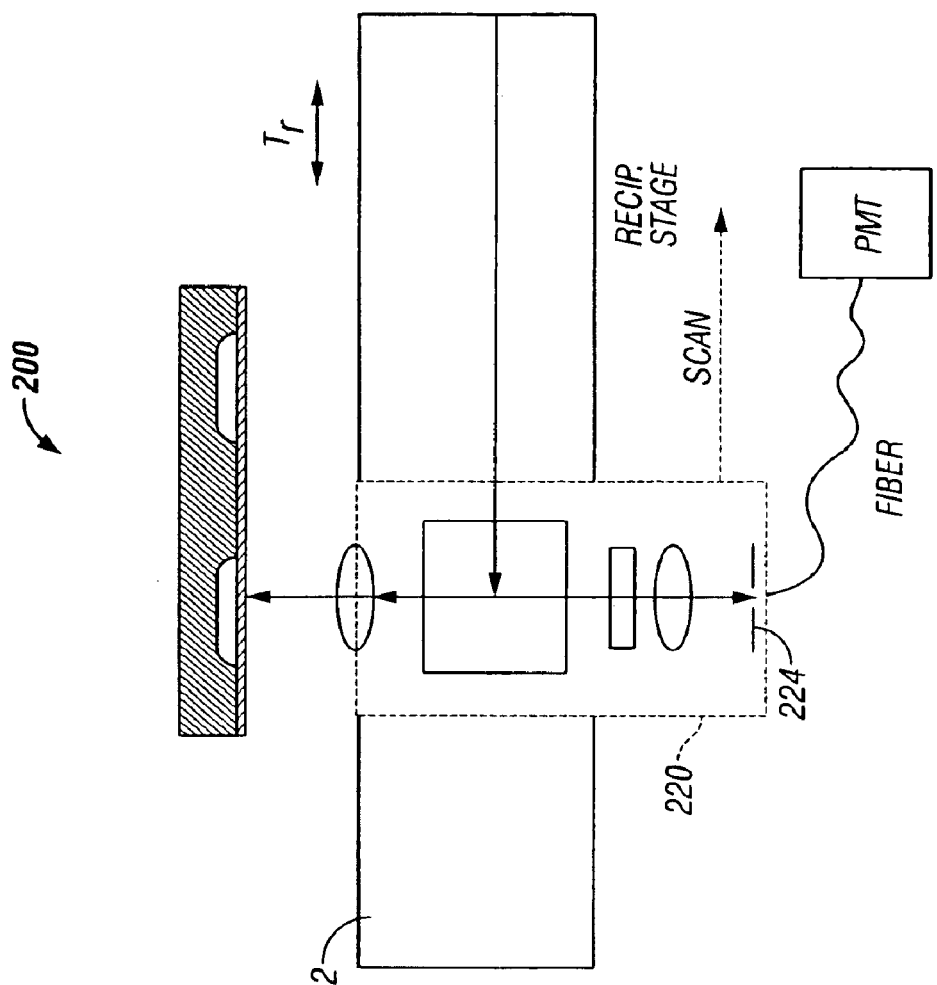
FIG. 12B is a side view of the system shown in FIG. 12A.
Figure 12A:
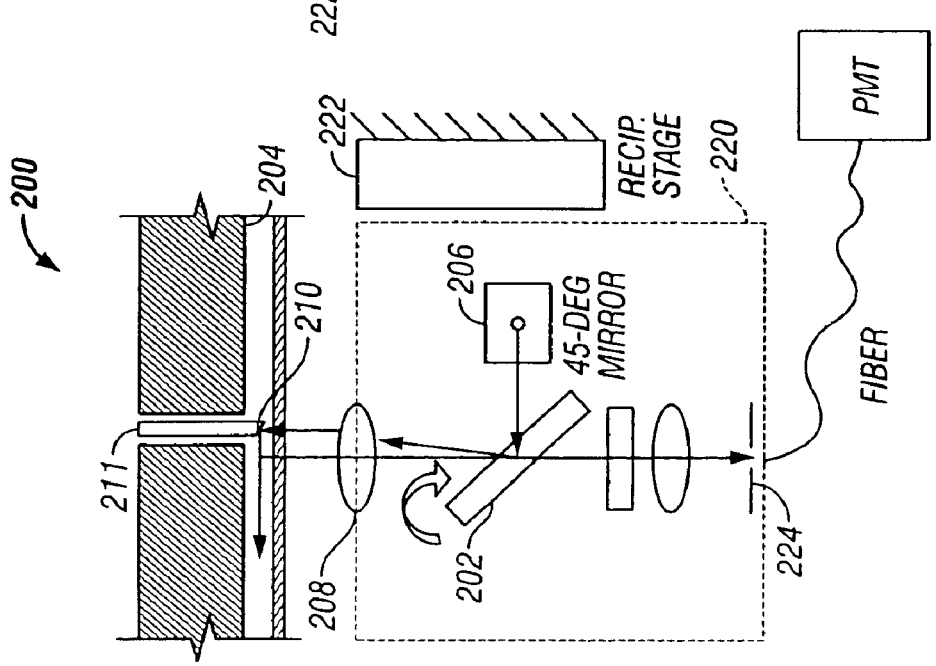
FIG. 12A is a front view of a system having a linearly movable stage to assist in directing light to a target region on a microfluidic device.

FIGS. 12A and 12B are side and front views respectively of another illumination and detection system (200) in accordance with the present invention. The illumination and detection system shown in FIGS. 12A and 12B includes a rotatable dichroic mirror (202) which serves to adjust the position of the beam in the vertical direction within a channel (204). In particular, the light beam is reflected off fixed mirror (206) towards rotatable mirror (202). The rotatable mirror (202) may be rotated to change the direction of the excitation beam. Lens (208) receives light from the mirror (202) and launches light towards a point on the reflective surface (210) of light directing member (211). Thus, when the rotatable mirror (202) is rotated, the point that the beam strikes the reflective surface (210) is moved a distance corresponding to the angle of the mirror (202). In this manner, the beam may be vertically positioned midway between the cover film and the opposing channel wall. As discussed above, it is desirable to position the beam in the vertical center of the channel to reduce background noise arising from light hitting the walls of the channel.

The illumination and detection system shown in FIGS. 12A and 12B also includes a movable optical head (220) which is adapted to move linearly along stage (222). The head (220) moves in the transverse direction Tr) relative to the channel (204) and thus, by moving the head along the stage, the beam may be aimed at various locations along the width of a channel as well as be aimed at different channels.

Collecting emitted light from the channels may be carried out as described above with respect to the other embodiments of the present invention. Also, an optical fiber may be added between slit (224) and the photomultiplier tube (226). This allows for the PMT or other detecting apparatuses to be separated or divorced from the optical head.

Figure 13:
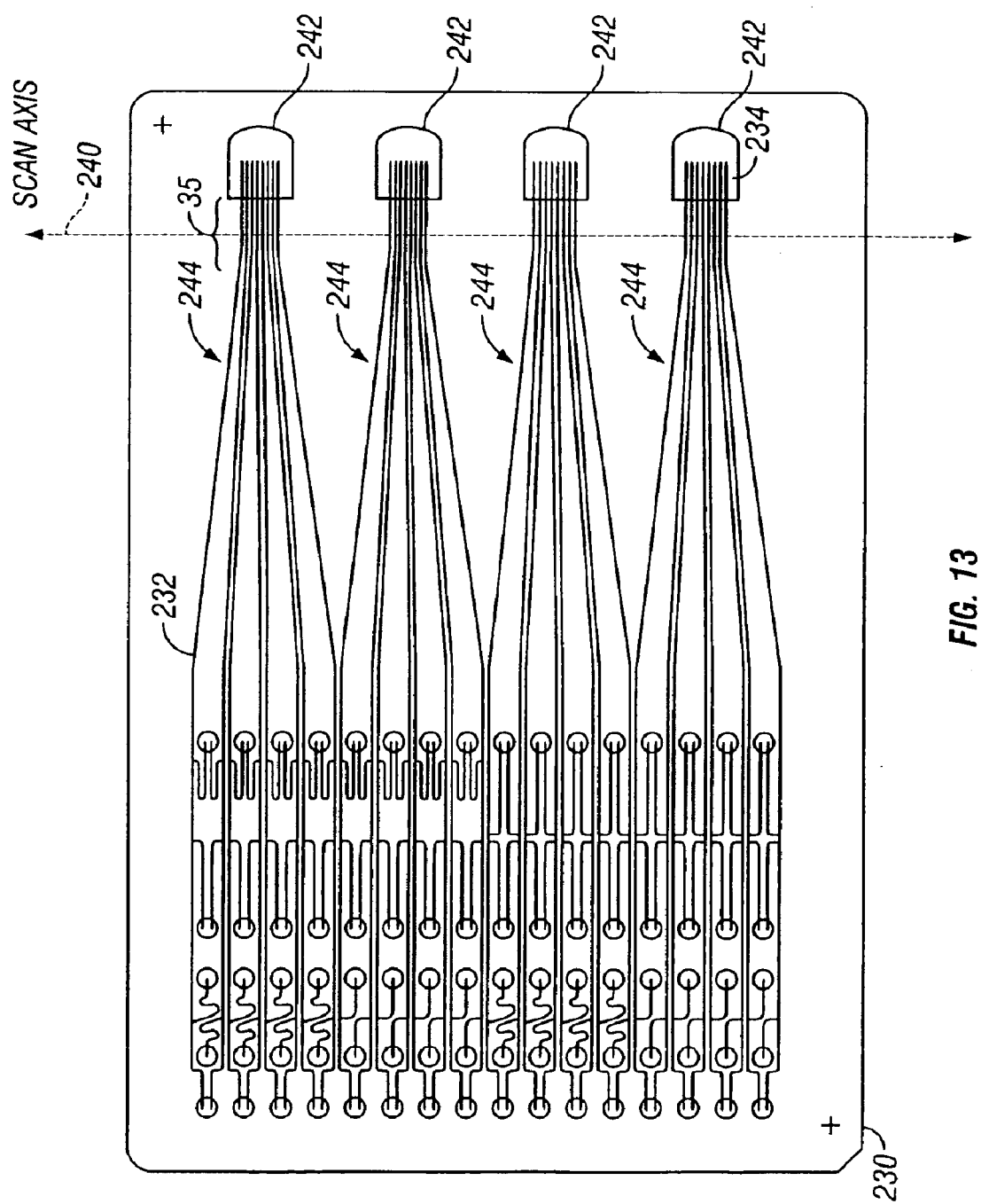
FIG. 13 shows a microfluidic device having a plurality of functional units. The functional units are aligned in the same direction.

FIG. 13 shows a microfluidic chip (230) having a plurality of channels (232) and functional units (244). Each of the functional units includes 8 separation channels (232) and a waste well (234). Amongst other things, the separation channels each have a detection channel portion (235) proximal to the waste well. The functional units are pointed in the same direction such that an optical head (not shown) may move along a single scan axis (240) to direct a beam into each channel for illumination and detection of materials. A light directing probe (242) may be positioned in each waste well (234). An excitation beam may be sequentially reflected off the light directing probes (242) and into the detection channel portions (235) as described in above embodiments. Also, collection and detection of the emitted light may be performed as described in the above embodiments.

The above described illumination and excitation systems may thus scan across one channel or across many channels. For example, 8 or more channels may be scanned. Also, the channels may be in close proximity. For example, the distance between channels may range from 0.05 to 10 mm, from 0.2 to 0.5 mm and perhaps be about 0.20 to 0.30 mm.

Figure 14A:
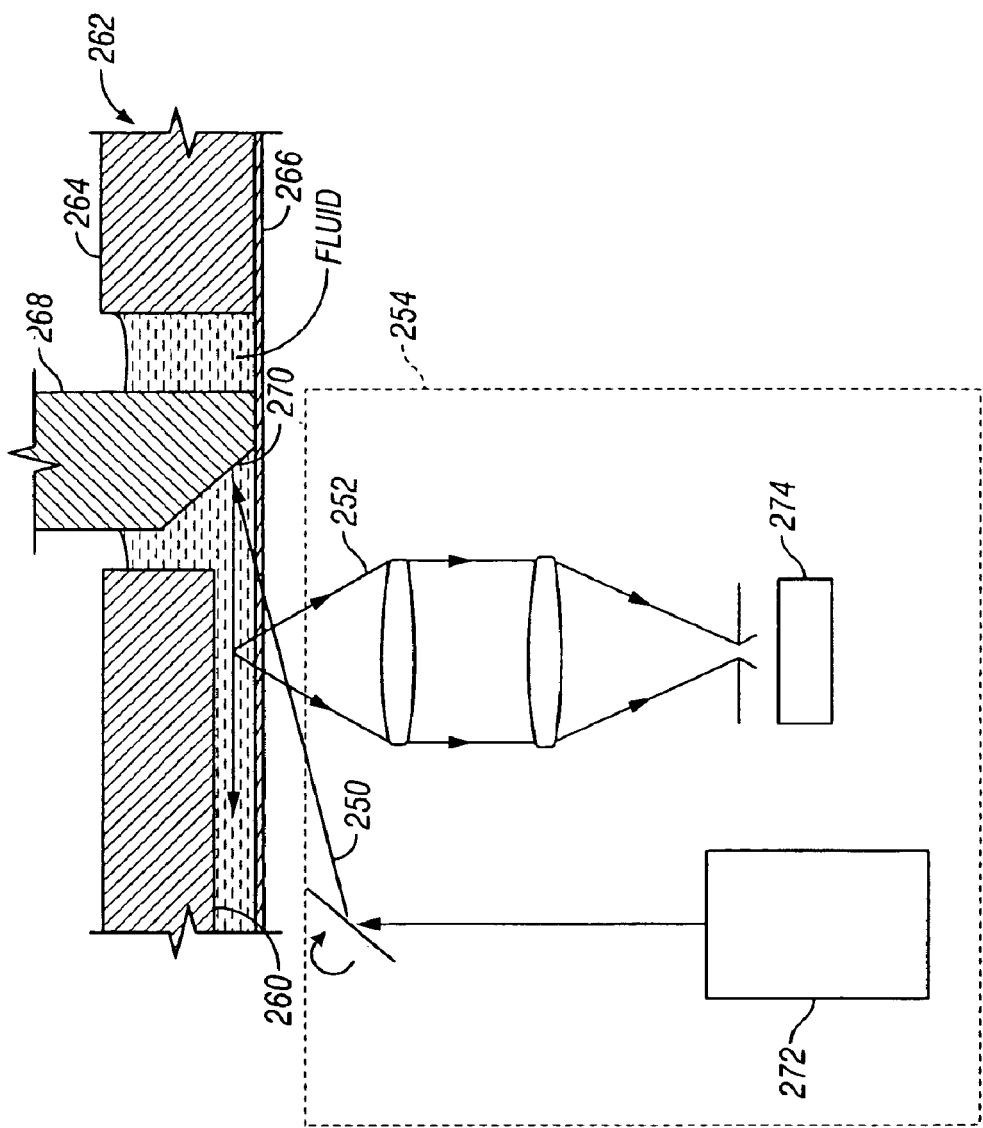
FIGS. 14A and 14B are schematic drawings of another system for illustrating and detecting material in a microfluidic device in accordance with the present invention.
Figure 14B:
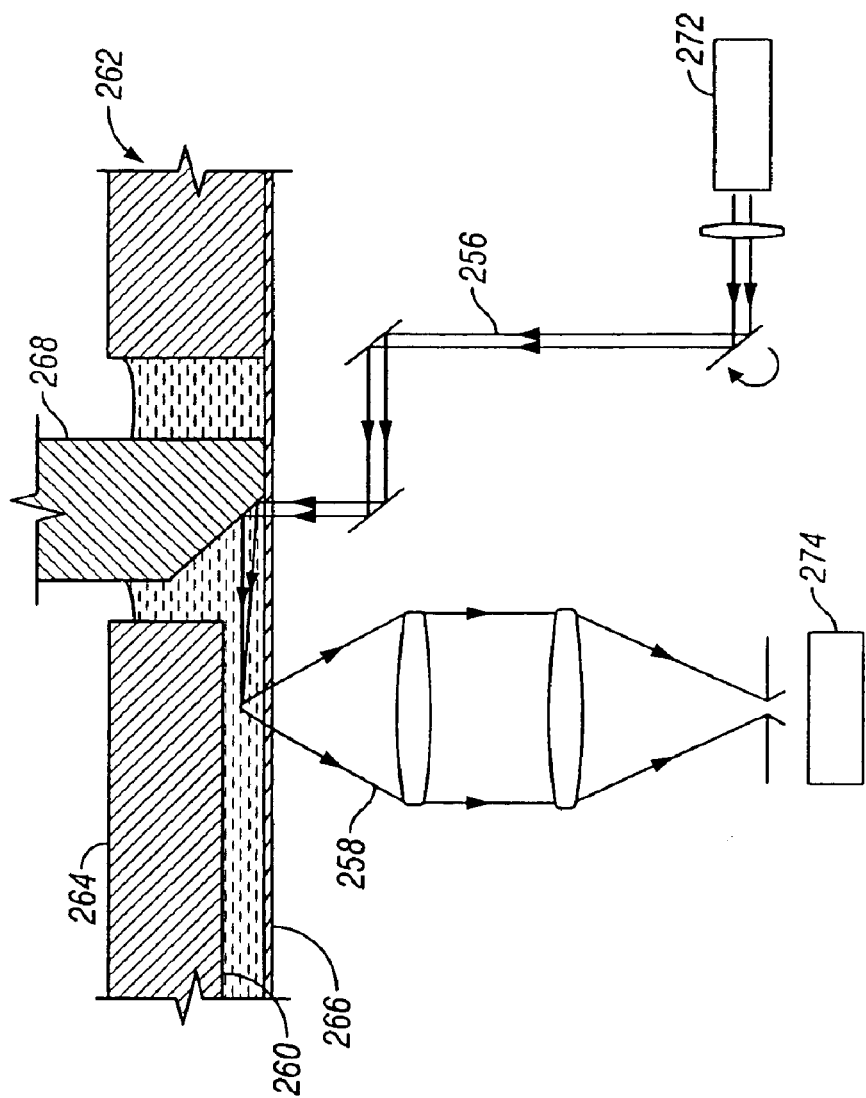

FIGS. 14A and 14B illustrate yet another configuration of a light illumination and detection system. As shown in these figures, the system may serve to illuminate a segment or zone of a channel (260) of a microfluidic device (262). As shown, the channel (260) is disposed in a body (264) and enclosed by a backing (266). A light-directing member (268) is positioned in a reservoir in fluid communication with the channel. The light-directing member includes a reflecting surface (270) to reflect the excitation beam down the channel. The excitation beam may be generated, for example, by a laser (272).

The light emitted from a fluorescent analyte or material in the detection zone (volume) is collected from a lens assembly and delivered through a slit to the PMT (274).

In the system shown in FIGS. 14A–14B, however, the light excitation and emission paths are separate. In FIG. 14A, the optical hardware is set up such that an excitation light beam (250) and emission light (252) have separate paths. Also, the optical hardware is shown housed in optical head (254). The set-up shown in FIG. 14B likewise provides separate paths for the excitation beam (256) and emission light (258). It is to be understood, however, that other configurations may be employed to keep the excitation and emission paths separate as is known to those having ordinary skill in art.

FIGS. 15A to 15D show various microfluidic chip designs which improve detection of fluorescent materials in microfluidic devices. In particular, the designs shown in FIGS. 15A to 15D reduce the phenomena of photobleaching. Photobleaching is a problem that arises when fluorescent materials are exposed to light for an extended period of time. The over-exposed materials become desensitized to light. Photobleaching in a microfluidic device may occur, for example, when the fluorescent materials to be detected are excited for an extended period of time upstream of the detection point. Consequently, when the fluorescent materials reach the detection point, the fluorescent materials emit less fluorescence and the overall sensitivity of the detection system is compromised. It is therefore desirable to minimize photobleaching.

Figure 15A:
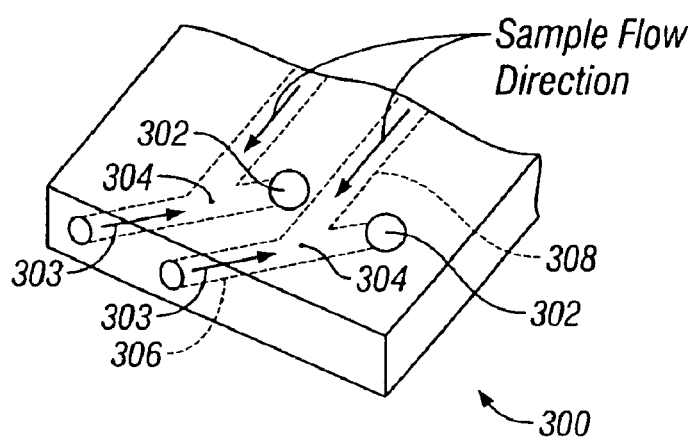
FIGS. 15A–15D show various channel configurations of a microfluidic device for reducing photobleaching.

FIG. 15A shows a microfluidic device (300) that reduces photobleaching. In particular, the device (300) includes a beam dump reservoir (302) which receives the excitation beam (303) after the excitation beam propagates through the detection point, zone, or region (304) in the waste channel (306). Another channel such as, for example, a separation channel (308) is joined to the waste channel at or near the detection point. The separation channel is joined at an angle such that the excitation beam (303) propagates through the detection zone (304) into the beam dump reservoir but does not enter the separation channel (308). Thus, sample and fluorescent materials traveling down the separation channel towards the detection point are not subject to the excitation light until they reach the detection zone (304). Photobleaching is thus reduced.

Additionally, the angle that the separation channel joins the waste channel may vary and may range from, for example, 10 to 170 degrees or perhaps, 30 to 150 degrees.

Figure 15B:
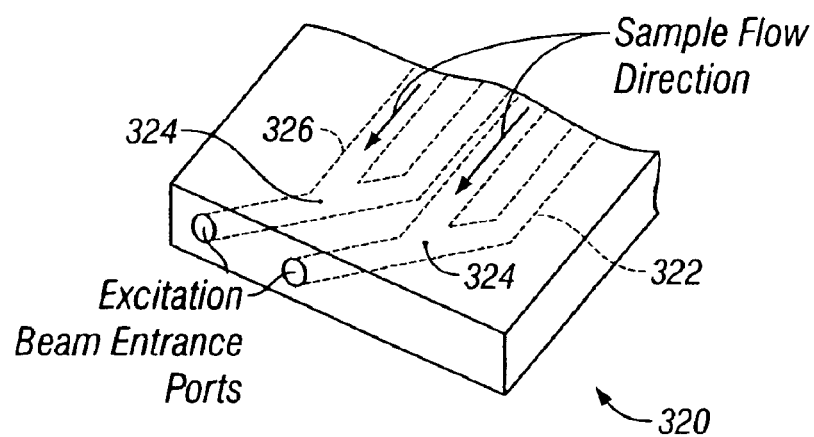

FIG. 15B shows another microfluidic device (320) that reduces photobleaching. Microfluidic device (320) includes a beam dump channel (322) instead of a beam dump reservoir as described in FIG. 15A. Again, the excitation beam propagates through the detection region (324) and into the beam dump channel (322). The sample materials, however, reach the detection point via another channel such as a separation channel (326) and thus, are not prematurely subject to the excitation beam. Photobleaching is thus reduced.

Figure 15C:
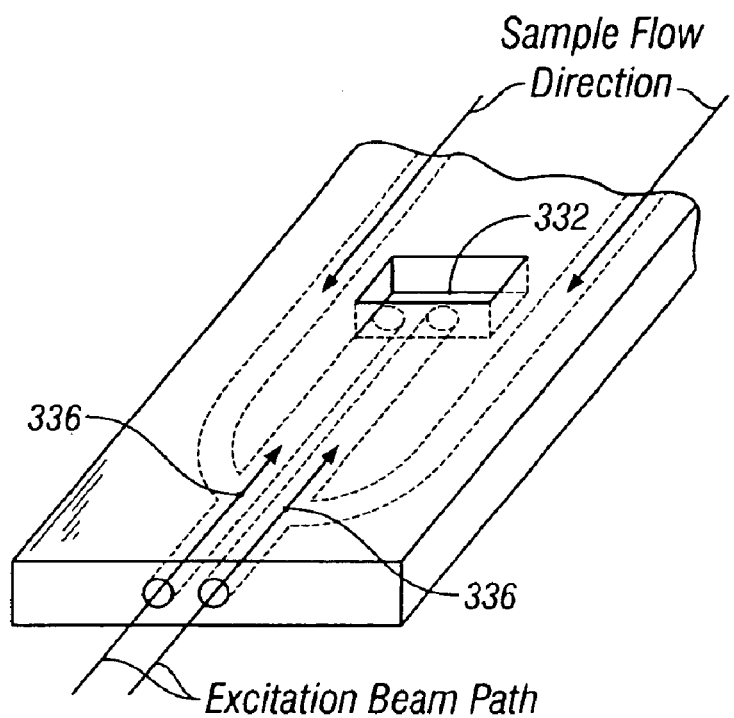
Figure 15D:
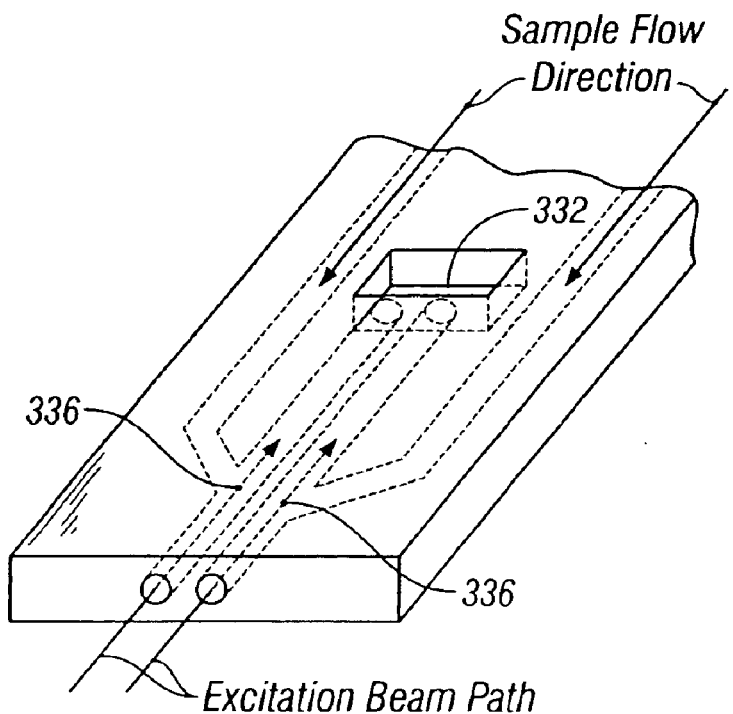

FIGS. 15C and 15D show additional configurations for reducing photobleaching in microfluidic devices. In these figures, a plurality of channels share a beam dump reservoir (332). In the devices shown in FIGS. 15C and 15D, the devices include two channels having a common beam dump reservoir. However, a beam dump reservoir may share more than two channels. As described above, second channels or separation channels may be connected to a beam dump channel at an angle such that the excitation beam passes through the detection point and does not enter the separation channel. In this manner, materials moving through the separation channel are not subject to the excitation beam until they reach the detection point (336).

Figures 16A, 16B:
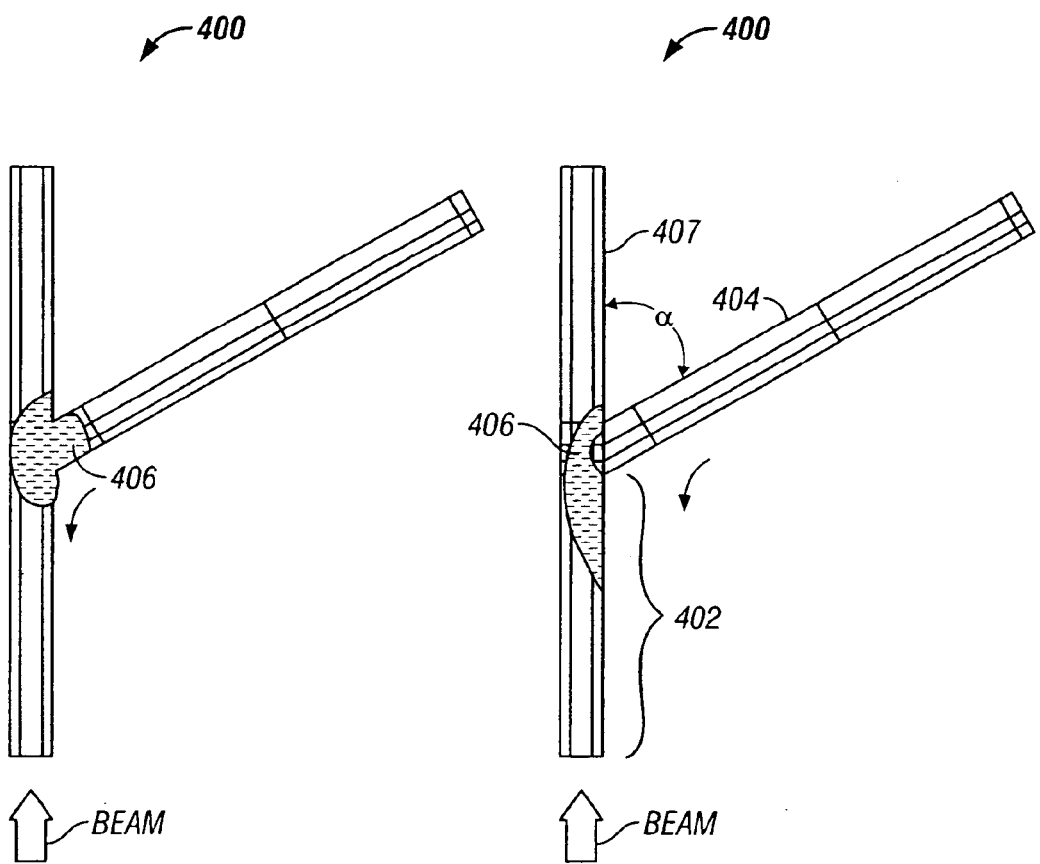
FIGS. 16A and 16B show a finite element model of a sample plug of material as it moves from a sample-flow channel to a sample-detection zone of another channel.

FIGS. 16A and 16B show a finite element computer simulations of the flow pattern of a sample as it moves from, for example, a separation channel into a waste channel. Note that the waste channel portion (402) is joined to separation or sample channel (404) at an angle (α) of 45 degrees.

The conditions were as follows for the computer simulation: the sample arm (404) had inlet boundary conditions of 7 A/m$^2$ current density; the buffer arm (407) had inlet boundary conditions of 0.7 A/m$^2$. This is about a 10/1 ratio. The outlet boundary condition was 0 volts. The buffer was water; the sample was 1 uM fluorescein in water. The fluorescein mobility was 4.4×10$^{-4}$ cm$^2$/V s. The initial condition for the sample was that of a peak that started as a 0.2 mm width, and traversed for 60 sec. in an electric field of 700 V/cm.

Referring to FIGS. 16A–16B, the sample plug (406) is shown elongated as it moves into the waste channel portion (402). Notably, the plug does not enter the buffer or beam dump channel (407) and the plug does not split. This computer example thus shows that the above channel constructs, given proper electric field strengths and other device parameters such as channel length, width, etc., can provide a device which serves to minimize photobleaching and properly move a sample plug from the separation channel, through the detection zone, and into the waste channel.

Also, it is to be understood that microfluidic devices of the present invention can include channels that serve purposes besides separation, sample flow and sample waste control. Indeed, the constructs set forth above for reducing photobleaching may be incorporated into microfluidic devices which use channels serving a wide variety of purposes including channels which serve purposes not explicitly recited herein.

Additional details as to the use or other aspects of the system described herein may be drawn from the background that is intended to form part of the present invention, including any of the patents and patent applications cited above, each of which being incorporated by reference herein in its entirety for any purpose. It is noted that this invention has been described and specific examples or variations of the invention have been portrayed. The use of those specific examples is not intended to limit the invention in any way. Additionally, to the extent that there are variations of the invention which are within the spirit of the disclosure and are equivalent to features found in the claims, it is the intent that the claims cover those variations as well. All equivalents are considered to be within the scope of the claimed invention, even those which may not have been set forth herein merely for the sake of relative brevity.

Also, the various aspects of the invention described herein, in any manner or section of the application including the Abstract, Field of the Invention, Background of the Invention, Summary of the Invention, Brief Description of the Drawings, the Drawings themselves and Detailed Description, may be claimed as set forth therein or be modified and/or used in combination with such other aspects also described to be part of the invention either explicitly, implicitly or inherently in order to form additional variations considered to be part of the invention. Furthermore, it is contemplated that any single or any combination of optional features of the inventive variations described herein may be specifically excluded from the invention claimed and be so-described as a negative limitation.

What is claimed is:

1. A system for use in the optical detection of sample material in a-channel of a microfluidic comprising:
    a microfluidic device having an opening in a first surface and at least one channel having a detection zone in fluid communication with said opening;
    a light-directing member separate from said microfluidic device, said member comprising a distal end, and a reflecting surface adjacent said distal end, said distal end being positionable within said opening such that when a light source is aimed at said reflecting surface, light reflects off said reflecting surface towards said detection zone within said at least one channel of said microfluidic device; and
    a detector positioned to receive non-reflected light from said detection zone.

2. The system of claim 1, wherein said light directing member comprises a prism.

3. The system of claim 2, wherein said prism includes a coated region providing said reflecting surface.

4. The system of claim 2, wherein said prism is adapted to provide said reflecting surface by total internal reflection.

5. The system of claim 2, wherein said light directing member further comprises a prism support.

6. The system of claim 5, wherein said prism support is adapted to function as an electrode.

7. The system of claim 2, wherein said prism is at least partially coated with a conductive material layer adapted to function as an electrode.

8. The system of claim 1, wherein said reflecting surface is oriented at an angle of 45° with respect to said first surface of said microfluidic device.

9. The system of claim 1, wherein said reflecting surface if provided around an axis perpendicular to said first surface of said microfluidic device.

10. The system of claim 1, wherein said light source is a laser.

11. The system of claim 1, further comprising a means for scanning light from said light source across said reflecting surface.

12. The system of claim 11, wherein said means for scanning light comprises a reflective member that moves to direct light at different detection zones.

13. The system of claim 1, wherein said light-directing member moves to direct light at different detection zones.

14. The system of claim 1, wherein said light-directing member rotates to direct light at different detection zones.

15. The system of claim 1, wherein said light-directing member is adapted to direct light at different detection zones when light is reflected at differing angular orientations.

16. The system of claim 15, wherein said light source rotates about an axis perpendicular to said first surface of said microfluidic device and through light-directing member.

17. The system of claim 1, wherein said microfluidic device further comprises a plurality of parallel channels and said system further comprises means to scan said light source across said plurality of channels.

18. The system of claim 1, wherein said detector collects light fluorescing from said sample material to be detected.

19. The system of claim 18, wherein said detector is a PMT.

20. The system of claim 1, further comprising a rotatable first reflector, said first reflector positioned in an optical path between said light source and said reflecting surface such that when said first reflector is rotated to an angle, said light reflected off said reflecting surface is moved by an amount corresponding to said angle of said first reflector.

21. The system of claim 20, comprising a rotating actuator that holds said first reflector.

22. The system of claim 21, wherein said rotating actuator is a galvanometer.

23. The system of claim 20, further comprising a rotatable second reflector positioned in said optical path between said first reflector and said reflecting surface, such that when said second reflector is rotated to an angle, said light reflected off said reflecting surface is moved by a distance corresponding to said angle of said second reflector.

24. The system of claim 23, further comprising a galvanometer to rotate said second reflector.

25. The system of claim 23, wherein said amount moved is in a vertical dimension perpendicular to the plane of said microfluidic device, and said distance moved is in a transverse dimension parallel to the plane of said microfluidic device and perpendicular to said at least one channel.

26. The system of claim 20, further comprising a lens positioned in said optical path between said first reflector and said reflecting surface of said light-directing member.

27. The system of claim 20, further comprising an optical head, said optical head holding said first reflector and said optical head being linearly movable such that when said optical head is moved to a location, said light-reflecting off said reflecting surface is moved by a distance corresponding to the location of said optical head.

28. The system of claim 20, wherein said detector detects emitted fluorescent light from illustrated samples in said at least one channel.

29. The system of claim 28, wherein said detector is divorced from said optical head.

30. The system of claim 29, wherein said detector is connected to said optical head via an optical fiber.

31. A method for the optical detection of material in a microfluidic device having a media contained therein, said method comprising:
submersing a distal end of a light-directing member in said media by positioning said member in an opening in a first surface of said microfluidic device;
directing light off a reflecting surface on said distal end towards a target region within a channel of said microfluidic device; and collecting non-reflected light from said target region.

32. A system for illuminating and detecting material in a microfluidic device comprising:
a microfluidic device comprising a body having first face and a second face opposite said first face and at least one channel in said second face, said body further having at least one hole extending from said first to said second face and said hole being in fluid communication with said at least one channel, said microfluidic device further comprising a cover bonded to said second face enclosing said at least one channel and forming a reservoir at said at least one hole;
a light-directing member separate from said microfluidic device, said light-directing member comprising a distal end, and a reflecting surface adjacent said distal end, said distal end positioned in said at least one reservoir of said microfluidic device wherein light from a light source directed at said reflecting surface reflects off said reflecting surface and through a detection portion of said at least one channel; and
a light collecting apparatus positioned to receive non-reflected light from said detection portion.

33. The system of claim 32, wherein said body defines an upper plane of said device and said cover defines plane of said device and wherein said light is directed at said reflecting surface of said first light-directing member from below said device.

34. The system of claim 32, wherein said body defines an upper plane of said device and said cover defines a lower plane of said microfluidic device and said light is directed at said reflecting surface of said first light-directing member from above said device.

35. The system of claim 33, wherein said light is directed towards said microfluidic device at a 90 degree to said cover.

36. The system of claim 32, wherein said microfluidic device is supported by a platen.

37. The system of claim 36, wherein said distal end of said light-directing member sets the position of said reflecting surface relative to said microfluidic device upon advancement to contact said cover and depressing said cover to said platten.

38. The system of claim 37, wherein said platen is recessed at a region opposite said light directing member.

39. The system of claim 32, wherein said microfluidic device comprises a plurality of channels portions oriented radially about said reservoir.

40. The system of claim 32, wherein said microfluidic device comprises a plurality of parallel channel portions and reservoirs in fluid communication with said channel portions and each of said reservoirs being adapted to receive a light-directing member.

41. The system of claim 32, wherein said light collecting apparatus collects fluorescent light emitted from a sample material to be detected.

42. The system of claim 41, further comprising a slit for imaging said collected light onto said light collecting apparatus, said slit being positioned in a path of said light to said light collecting apparatus.

43. The system of claim 42, wherein said light collecting apparatus is a PMT.

44. The system of claim 32, wherein said microfluidic device comprises a sample-flow channel fluidly connected to said at least one channel at said detection portion of said at least one channel, said sample-flow channel forming an angle with said at one channel such that light propagating through said at least one channel towards said detection portion illuminates material held within said detection portion and continues through said at least one channel such that substantially no light enters said sample-flow channel.

45. The system of claim 44, wherein said angle ranges from 30 to 60 degrees.

46. The system of claim 44, wherein said at least one channel comprises a plurality of channels, each of said channels being fluidly connected to a sample-flow channel at said detection portion, said sample-flow channel forming an angle with each of said plurality of channels such that light propagating through said channel towards said detection portion illuminates material held within said detection portion and continues through said at least one channel such that substantially no light enters said sample-flow channel.

47. The system of claim 46, wherein each of said sample-flow channels connects to a beam-dump reservoir.

48. The system of claim 47, comprising a plurality of beam-dump reservoirs and wherein each of said sample-flow channels fluidly connect to a separate beam-dump reservoir.

* * * * *

UNITED STATES PATENT AND TRADEMARK OFFICE
CERTIFICATE OF CORRECTION

| | |
|---|---|
| PATENT NO. | : 6,900,889 B2 |
| APPLICATION NO. | : 10/739720 |
| DATED | : May 31, 2005 |
| INVENTOR(S) | : Bjornson et al. |

It is certified that error appears in the above-identified patent and that said Letters Patent is hereby corrected as shown below:

On the title page: Item [75] the third inventor's name should read
-- Michael Robert Gluszczak --.

Signed and Sealed this

Twenty-ninth Day of July, 2008

JON W. DUDAS
*Director of the United States Patent and Trademark Office*